US00PP17062P2

(12) United States Plant Patent
Olesen

(10) Patent No.: US PP17,062 P2
(45) Date of Patent: Aug. 29, 2006

(54) CLIMBING ROSE PLANT NAMED 'POULCY010'

(50) Latin Name: ***Rosa* hybrid**
Varietal Denomination: Poulcy010

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 178 days.

(21) Appl. No.: 11/002,549

(22) Filed: Dec. 1, 2004

(51) Int. Cl.
*A01H 5/00* (2006.01)

(52) U.S. Cl. ..... Plt./114
(58) Field of Classification Search ..... Plt./114
See application file for complete search history.

*Primary Examiner*—Anne Marie Grunberg
*Assistant Examiner*—Annette H Para

(57) ABSTRACT

A new garden rose plant of the climbing rose class which has abundant, pink flowers and attractive foliage. This new and distinct variety has shown to be uniform and stable in the resulting generations from asexual propagation.

1 Drawing Sheet

Botanical classification: *Rosa* hybrid.
VARIETY DENOMINATION: 'Poulcy010'.

SUMMARY OF THE INVENTION

The present invention constitutes a new and distinct variety of garden rose plant, of the climbing rose class, that originated from a controlled crossing between the female seed parent 'Meidomonac', described and illustrated in U.S. Plant Pat. No. 5,105 issued Sep. 20, 1983, and the male pollen parent, an unnamed seedling.

The two parents were crossed during the summer of 1990 and the reuslting seeds were planted in a controlled environment in Fredensborg, Denmark. The new variety is named 'Poulcy010'.

The new variety may be distinguished from its female seed parent, 'Meidomonac' by the following combination of characteristics:

1. While the seed parent 'Meidomonac' is a low growing shrub rose plant, 'Poulcy010' is a climbing rose plant.
2. While the seed parent has a petal count of 53, 'Poulcy010' has 65 to 70 petals.
3. While the seed parent 'Meidomonac' has a petal color upon opening, upper surface of Red Group 55C the same characteristic of 'Poulcy010' is Red Group 49C.

The new variety may be distinguished from the male pollen parent, by the following combination of characteristics:

1. While the pollen parent has dark pink flowers 'Poulcy010' has light pink flowers.
2. While the pollen parent has double flowers the same of 'Poulcy010' are semi-double.
3. While the unnamed pollen parent has medium sized flowers those of 'Poulcy010' are small.

The objective of the hybridization of this rose variety was to create a new and distinct variety for garden use with unique qualities, such as:

1. Uniform and abundant light pink flowers;
2. Vigorous, but compact growth when propagated both as a budded rose and on its own roots;
3. Disease resistance.

4. Reduced apical dominance in flowering habit. The new variety consistently produces flowers evenly from the lower branches to the top of the plant.

This combination of qualities is not present in previously available commercial cultivars of this type, known to the inventors, and distinguish 'Poulcy010' from all other varieties of which we are aware.

As part of the rose development program, Mogens N. Olesen germinated the seeds from the aforementioned hybridization during winter of 1990 and conducted evaluations on the resulting seedlings in a controlled environment in Fredensborg, Denmark.

'Poulcy010' was selected in the spring of 1991 by the inventors as a single plant from the progeny of the aforementioned hybridization.

Asexual reproduction of 'Poulcy010' by traditional budding and rooted cuttings was first done by Mogens N. Olesen in the nursery in Fredensborg, Denmark in July, 1991. This initial and other subsequent asexual propagations conducted in controlled environments have demonstrated that the characteristics of 'Poulcy010' are true to type and are transmitted from one generation to the next.

BRIEF DESCRIPTION OF THE DRAWING

The accompanying color illustration shows as true is reasonably possible to obtain in color photographs of this type, the typical characteristics of the buds, flowers, leaves, and stems, of 'Poulcy010'. Specifically illustrated in the drawing.

DETAILED DESCRIPTION OF THE VARIETY

Figures 1A, 1B, 1C, 1D, 1E, 1F:
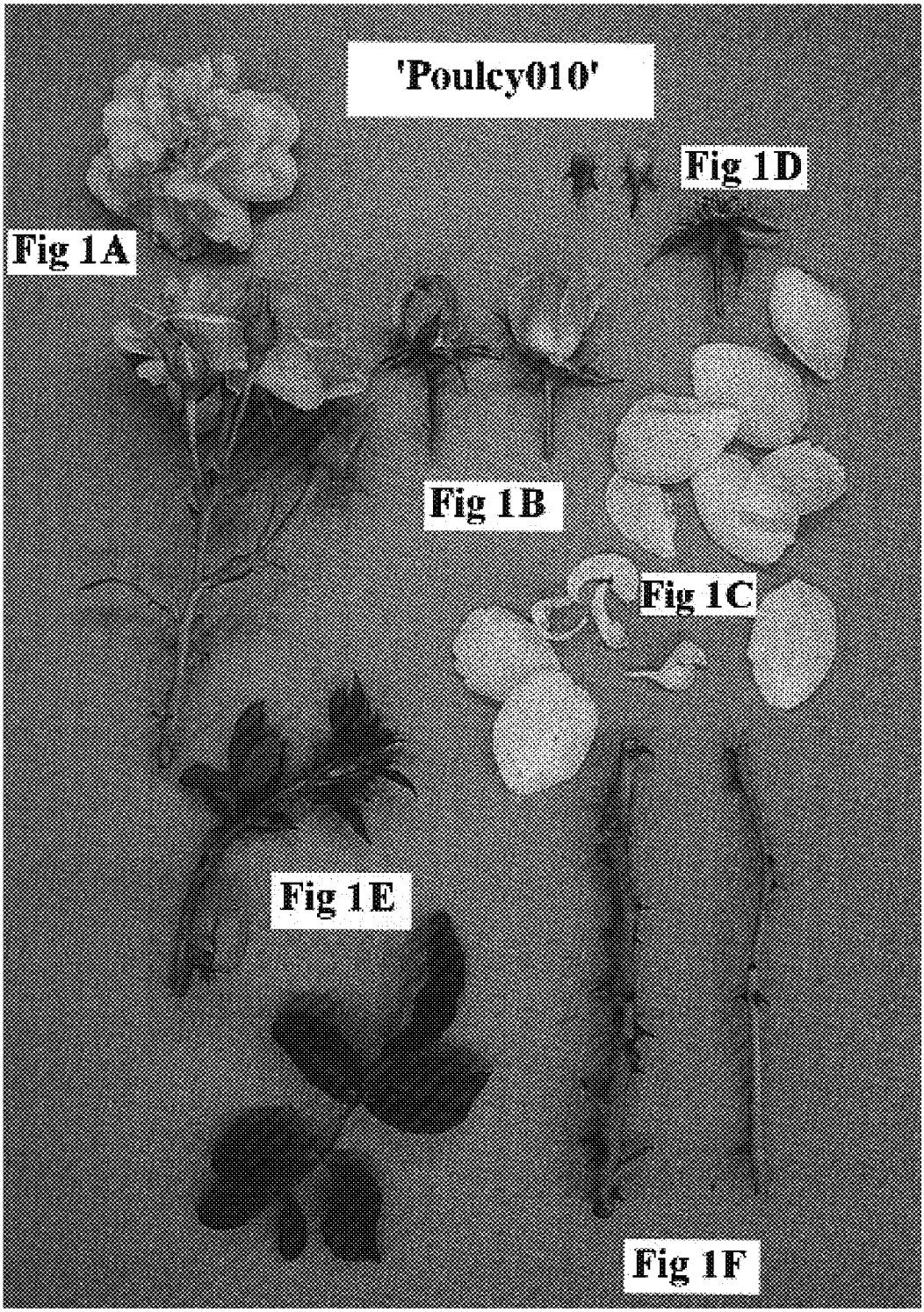
FIG. 1A; Open flower, cluster of open flowers showing branching, and the attachment of leaves, buds, and peduncles FIG. 1B; Partially opened flowers.
FIG. 1C; Flower petals, detached.
FIG. 1D; Sepals detached, and sepals attached to receptable, showing reproductive flower parts.
FIG. 1E; Juvenile growth and mature leaf.
FIG. 1F; Bare stems exhibiting prickles.

The following is a description of 'Poulcy010', as observed in its growth in in a field nursery in Jackson County, Oreg. Observed plants are 2 years of age, and were grown on *Rosa multiflora* understock. Color references are made using The Royal Horticultural Society (London, England) Colour Chart, 1995, except where common terms of color are used.

For a comparison, several physical characteristics of the rose variety 'Poulskab', a rose variety from the same inventors described and illustrated in U.S. Plant patent application Ser. No. 10/268,149 (abandoned) dated Dec. 18, 2003, are compared to 'Poulcy010' in Chart 1.

CHART 1

| | 'Poulcy010' | 'Poulskab' |
|---|---|---|
| General tonality. | Red Group 56B to 49A. | Red Group 54D. |
| Flower bud size, upon opening. | 10 mm. | 15 mm. |
| Flower diameter | 50 mm. | 50 to 60 mm. |

FLOWER AND FLOWER BUD

Blooming habit: Continuous.

Flower bud:

*Size.*—Upon opening, 15 mm in length from base of receptacle to end of bud. Average bud diameter is 10 mm.

*Bud form.*—Urceolate.

*Bud color.*—As the sepals unfolded, petals are Red Group 36A with blended intonations of Red Group 38B. Distinct intonations of Green-White Group 157A to Yellow-Green Group 145D observed.

*Sepal inner surface.*—Color: Yellow-Green Group 146A blending with Green Group 142A. Toward the point of attachment, very light anthocyanic intonations of Greyed-Red Group 181C. Surface: Weak pubescence observed.

*Sepal outer surface.*—Color: Yellow-Green Group 144A. Anthocyanic pigments at margins and mid vein the color of Greyed-Red Group 181B observed. Texture: Rough due to the presence of numerous stipitate glands.

*Sepal shape.*—Apex: Cirrhose. Base: Flat at union with receptacle.

*Sepal margin.*—Margins have strong foliaceous appendages on three of the five sepals.

*Sepal size.*—Normally 20 mm (l) by 5 mm (w).

*Receptacle.*—Texture: Smooth. Shape: Urn-shaped. Size: Normally 6 mm (l)×10 mm (w). Color: Yellow-Green Group 144A. Light anthocyanic pigments the color of Greyed-Red Group 182B observed.

*Pedicel.*—Length: 25 to 40 mm. Diameter: 1.5 to 2 mm. Color: Yellow-Green Group 144B. Anthocyanic pigment Greyed-Red 182A. Strength: Medium strength.

Flower bud development: Flower buds are borne in clusters of 5 to 21 flower buds per flowering stem. Inflorescence type is a raceme. Reduced apical dominance in flower habit causes flower buds develop evenly from the base of the plant to the upper branches.

Flower bloom:

*Fragrance.*—None.

*Duration.*—The blooms have a duration on the plant of approximately 7 to 10 days. Petals fall cleanly away from plant after flowers have fully matured.

*Size.*—Flower diameter is 50 mm on average when open. Flower depth is 20 mm on average.

*Flower shape.*—General shape is a loose rosette with petals of different sizes.

*Shape of flower, side view.*—Upon opening, Upper portion: Convex. Lower portion: Flat. After opening, Upper portion: Flattened convex. Lower portion: Concave.

Petalage. Under normal conditions, flowers have 65 to 70 petals total, 20 to 25 of which are petaloids.

*Petal color.*—Upon opening, outer petals Upper surface: Red Group 49C. Lower surface: Red Group 55C to 55D. Upon opening, inner petals: Upper surface: Red Group 38C to Red Group 49B. Lower surface: Red Group 55C. Basal petal spots, upon opening: Upper surface: Yellow Group 4C to 4D. Lower surface: Yellow Group 4D to Yellow-Green Group 150D. After opening, outer petals Upper surface: Red Group 55D. Occasionally the upper surface exhibits streaks of Red-Purple Group 57A. Lower surface: Red Group 55C to 55D. After opening, inner petals: Upper surface: Red Group 55D. Occasionally the upper surface exhibits streaks of Red-Purple 57A. Lower surface: Red Group 55C to 55D. Basal petal spots, after opening: Upper surface: White Group 155A to Yellow-Green Group 150D. Lower surface: White Group 155A to Yellow-Green Group 150D.

General tonality: On open flower Red Group 56B to Red Group 49A. No change in the general tonality at the end of the 10th day. Afterwards, general tonality is White Group 155A.

Petals:

*Petal reflex.*—Somewhat reflexed,

*Margin.*—Medium undulations of margin observed. Margins are entire with an occasional cleft or point at the center of the apex.

*Shape.*—Generally narrow elliptical in shape. Apex: Rounded and occasionally cuspidate. Base: Acute.

*Size.*—Outermost petals: 29 mm (l)×21 mm (w). Innermost petals: 23 mm (l)×11 mm (w).

*Texture.*—Smooth.

*Thickness.*—Thin.

Petaloids:

*Quantity.*—20 to 25.

*Shape.*—Very irregular. Linear and somewhat crescent shaped.

*Color.*—Upper surface: Red Group 55D. Lower surface: Red Group 55C to 55D.

*Size.*—6 to 15 mm (l)×3 to 10 mm (w).

Reproductive organs:

*Pollen.*—None observed.

*Anthers.*—Size: 2 mm in length. Color: Greyed-Yellow 160B with margins of Greyed-Orange 163A. Quantity: 25 on average.

*Filaments.*—Color: Yellow-Green Group 149D. Length: 2 to 4 mm.

*Pistils.*—Length: 6 mm. Quantity: 35 on average.

*Stigmas.*—Superior in location relative to the length of the filaments and the height of the anthers. Color: Greyed-Yellow 160D.

*Styles.*—Color: Greyed-Red Group 178D.

*Hips.*—None Observed in the field nursery in Jackson County Oreg.

PLANT

Plant growth: Climbing. When grown as a budded field grown plant on *Rosa multiflora* understock, the average height of the plant is 150 to 200. Average spread is 100 cm.

Stems:

*Color.*—Juvenile growth: Yellow-Green Group 145B with anthocyanic intonations of Greyed-Red Group 181B. Mature growth: Yellow-Green Group 145B.

*Length.*—On average, canes are 150 cm from the base of the plant to the flowering portion.

*Diameter.*—12 mm.

*Internodes.*—On mature canes, there is an average distance of 44 mm between nodes.

*Surface texture.*—Young wood: Smooth. Older wood: Smooth.

Thorns:

*Incidence.*—8 thorns per 10 cm of stem.

*Shape.*—Upper side: Flat. Lower side: Deeply concave.

*Juvenile thorns.*—Color: Greyed-Red Group 181A.

*Mature thorns.*—Color: Greyed-Red Group 181A to 181B with intonations of Greyed-Yellow Group 162A.

Plant foliage: Normal number of leaflets leaves in middle of the stem: 7 leaflets.

*Compound leaf.*—120 mm (l)×70 (w).

*Quantity.*—2 leaves per 10 cm of stem on average.

*Color of mature foliage.*—Upper side: Yellow-Green Group 147A. Lower side: Yellow-Green Group 147B.

*Color of juvenile foliage.*—Upper side: Yellow-Green Group 146B. Margins are Greyed-Purple 185A. Lower side: Yellow-Green Group 146D. Anthocyanic intonations of Greyed-Red 181A generalized in location.

Plant leaves and leaflets:

*Stipules.*—Size: 18 mm in length. Shape: Linear, slightly broad based with outward extending apecies. Margins: Finely serrated with few stipitate glands. Color: Yellow-Green Group 144A.

*Petiole.*—Length: 26 mm. Diameter: 1.5 mm.

*Upper surface.*—Color: Yellow-Green Group 146B with Greyed-Red Group 178C.

*Lower surface.*—Color: Yellow-Green Group 145B.

*Observations.*—Few stipitate glands and on upper surface.

*Rachis.*—Length: 50 mm. Upper surface: Color: Yellow-Green Group 146B. Lower surface: Color: Yellow-Green Group 145B. Observations: Shallow prickles observed on the undersurface.

*Leaflet.*—Edge: Serrated. Size: Average size of the terminal leaflet on normal leaves is 45 mm in length by 20 mm wide. Shape: Generally elliptical. Base: Acuminate. Apex: Acuminate. Texture: Smooth. Thickness: Average. Arrangement: Odd pinnate. Venation: Reticulate. Glossiness: Matte finish.

Disease resistance: Above average resistance to powdery and downy mildew, rust, black spot, and Botrytis under normal growing conditions in Jackson County, Oregon.

Cold Hardiness: The variety 'Poulcy010' has been found to be Cold tolerant to USDA cold Hardiness Zone 6.

What is claimed is:

1. A new and distinct variety of rose plant of the climbing rose class named 'Poulcy010', illustrated and described herein as a distinct and novel rose variety due to its abundant pink flowers, disease resistance, and extended period of bloom.

* * * * *

'Poulcy010'